United States Patent

Buongiorne et al.

(10) Patent No.: US 6,509,143 B2
(45) Date of Patent: *Jan. 21, 2003

(54) CONCENTRATED PHOTOGRAPHIC COLOR DEVELOPING COMPOSITION CONTAINING STAIN REDUCING AGENT

(75) Inventors: Jean M. Buongiorne, Brockport, NY (US); Ramanuj Goswami, Webster, NY (US); Mary E. Craver, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/896,698

(22) Filed: Jun. 29, 2001

(65) Prior Publication Data

US 2002/0061474 A1 May 23, 2002

Related U.S. Application Data

(63) Continuation-in-part of application No. 09/679,922, filed on Oct. 5, 2000.

(51) Int. Cl.$^7$ ............................................... G03C 7/413
(52) U.S. Cl. ....................................................... 430/466
(58) Field of Search ......................................... 430/466

(56) References Cited

U.S. PATENT DOCUMENTS

| 4,525,451 A | 6/1985 | Ohki et al. ................. 430/551 |
| 4,900,651 A | 2/1990 | Ishikawa et al. ............ 430/380 |
| 6,077,651 A * | 6/2000 | Darmon et al. ............. 430/434 |
| 6,136,518 A | 10/2000 | Buongiorne et al. ........ 430/486 |
| 6,153,364 A | 11/2000 | Goswami et al. ........... 430/434 |
| 6,153,365 A | 11/2000 | Goswami et al. ........... 430/434 |
| 6,228,567 B1 | 5/2001 | Darmon et al. ............. 430/486 |
| 6,232,053 B1 | 5/2001 | Goswami et al. |

FOREIGN PATENT DOCUMENTS

| EP | 1 109 063 A1 | 6/2001 |
| WO | WO 97/10887 | 3/1997 |

* cited by examiner

*Primary Examiner*—Hoa Van Le
(74) *Attorney, Agent, or Firm*—J. Lanny Tucker

(57) ABSTRACT

Concentrated aqueous photographic color developing compositions include a photographic color developing agent in free base form and a compound represented by Structure I

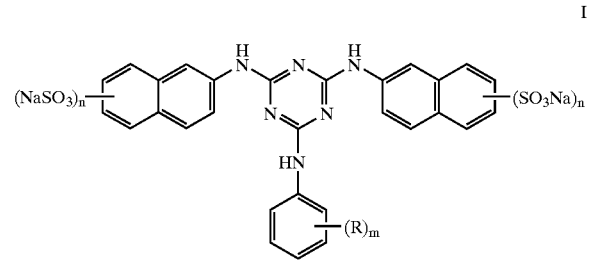

wherein R is carboxy or sulfo, m is an integer of from 0 to 7, and n is an integer of from 2 to 5. These compositions can be used to provide images in color silver halide photographic materials with reduced residual sensitizing dye stain.

18 Claims, No Drawings

CONCENTRATED PHOTOGRAPHIC COLOR DEVELOPING COMPOSITION CONTAINING STAIN REDUCING AGENT

RELATED APPLICATIONS

This is a Continuation-in-part of recently allowed and commonly assigned U.S. Ser. No. 09/679,922 (filed Oct. 5, 2000 by Goswami, Buongiorne, and Craver).

FIELD OF THE INVENTION

This invention relates to novel photographic processing compositions. In particular, it relates to concentrated photographic color developing compositions that reduce stain resulting from residual sensitizing dyes. This invention is useful in the photographic industry.

BACKGROUND OF THE INVENTION

The conventional image-forming process of silver halide photography includes imagewise exposure of a photographic silver halide recording material to actinic radiation (such as visible light), and the eventual manifestation of a useable image by wet photochemical processing of that exposed material. A fundamental step of photochemical processing is the treatment of the material with one or more developing agents to reduce silver halide to silver metal. With black-and-white photographic materials, the metallic silver usually comprises the image. With color photographic materials, the useful image consists of one or more organic dye images produced from an oxidized color developing agent formed wherever silver halide is reduced to metallic silver.

To obtain useful color images, it is usually necessary to remove all of the silver from the photographic element after color development. This is sometimes known as "desilvering". Removal of silver is generally accomplished by oxidizing the metallic silver, and then dissolving it and undeveloped silver halide with a "solvent" or fixing agent in what is known as a fixing step. Oxidation is achieved using an oxidizing agent, commonly known as a bleaching agent. For some processing methods, these two functions can be performed in the same processing step in what is known as bleach-fixing.

Color photographic silver halide materials often contain various spectral sensitizing dyes that extend the inherent photosensitivity of the photosensitive silver halide emulsions to electromagnetic radiation. One important class of such spectral sensitizing dyes includes carbocyanine sensitizing dyes that are commonly included in silver halide emulsion layers in photographic silver halide films. For example they are often present in color reversal photographic silver halide films (films normally used to provide color positive images).

Many photographic silver halide elements contain residual spectral sensitizing dyes after photoprocessing. In some cases, the level of retained spectral sensitizing dyes is inconsequential and thus, unobservable. In other instances, however, the high level of retained spectral sensitizing dye results in undesirably high dye stain (or unwanted color) in the elements. This dye stain problem is aggravated when the silver halide elements are designed for shorter wet processing times, or when certain silver halide emulsions are used that require higher concentrations of sensitizing dyes.

A number of solutions have been proposed for this problem, including the inclusion of common water-soluble stilbene optical brighteners, such as diaminostilbene compounds, in various photographic processing compositions. For example, such compounds are known to be used in color developer compositions [as described for example, in Research Disclosure, 20733, page 268, July, 1981 and U.S. Pat. No. 4,587,195 (Ishikawa et al.) and as commonly used in the commercial Process RA-4 color developing compositions available from a number of manufacturers], bleach-fixing compositions [as described for example, in JP Kokai 1-062642 (published Mar. 9, 1989), JP Kokai 1-158443 (published Jun. 21, 1989), and U.S. Pat. No. 5,043,253 (Ishikawa)], or dye stabilizing compositions used at the end of the color photographic photoprocessing [as described for example in U.S. Pat. No. 4,895,786 (Kurematsu et al.)].

Concentrated and working strength fixing compositions that solve the residual dye stain problem are described in U.S. Pat. No. 6,013,425 (Craver et al.). These compositions contain certain triazinylstilbene compounds as stain reducing agents. While they are quite effective in this regard, keeping them in solution may require the presence of one or more water-soluble stabilizing compounds such as glycols.

The problems with residual sensitizing dyes have also been satisfactorily addressed by incorporating certain stain reducing agents into one or more working strength photographic processing compositions. These compounds are described in U.S. Pat. No. 6,153,365 (Goswami et al.) and U.S. Pat. No. 6,153,364 (Goswami et al.) as colorless or slightly yellow compounds having an extended planar $\pi$ system that is devoid of a diaminostilbene fragment or fused triazole nuclei. While these compounds can be incorporated into various photoprocessing compositions, it is preferred to include them in concentrated photographic processing compositions.

A preferred class of solubilized stain reducing agents are used in the concentrated fixing photographic fixing compositions described in U.S. Ser. No. 09/680,385 (filed Oct. 5, 2000 by Buongiorne, Craver, and Goswami).

However, when we attempted to incorporate some of these stain reducing agents into concentrated solutions such as concentrated color developing solutions, we found that some of them did not pass our rigorous solubility tests. For example, many of them showed unacceptable solubility even when organic solvents were added, insolubility in solution at low temperature for lengthy times, or insolubility in concentrated color developing compositions.

There remains a need in the photographic industry for a way to decrease the dye stains resulting from retained sensitizing dye during color development using concentrated color developing compositions that meet all manufacturing, customer use, and storage stability requirements.

SUMMARY OF THE INVENTION

The problems noted above are overcome using a concentrated aqueous color developing composition having a pH of from about 11 to about 13 and comprising:

a) at least 0.08 mol/l of a color developing agent in free base form, and b) at least 0.009 mol/l of a compound having the Structure I:

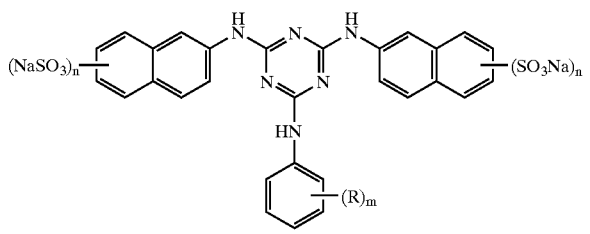

wherein R is carboxy or sulfo, m is an integer of from 0 to 5, and n is an integer of from 2 to 7.

In addition, the present invention includes a method for providing a color image comprising color developing an imagewise exposed color silver halide photographic element using the concentrated aqueous color developing composition described above with or without dilution.

The advantages of this invention are several. The compounds that are used as spectral sensitizing dye stain reducing agents are highly soluble in concentrated aqueous color developing compositions. Their inherent fluorescence is relatively less than known compounds so that fluorescence is not a problem when the compound cannot be removed from the photographic material or processing composition.

Only the specific stain reducing agents represented by Structure I provide the desired stability in the concentrated aqueous color developing compositions of this invention. Thus, the compounds of Structure I have low temperature solubility that is determined by placing 100 ml aqueous samples of the compounds in closed containers and holding them individually it at 0° F. (−18° C.), 20° F. (−7° C.), 30° F. (−1° C.), 40° F. (4° C.) and 50° F. (10° C.) for 14 days and then observing the samples 24 hours later for signs of precipitation or other observable changes (for example color, presence of haze, or phase separation).

Working strength color developing compositions can be prepared using the concentrated composition of the present invention by diluting them in an appropriate manner for photoprocessing use. Alternatively, the concentrated composition of this invention can be used "as is", without dilution.

DETAILED DESCRIPTION OF THE INVENTION

For obtaining color images, photographic processing methods include at the least, a color development step, a bleaching step, a fixing step (or a combined bleach-fixing step), and a rinsing or color stabilizing step. Some of the processing methods will include additional steps, for example a black-and-white developing step and pre-bleaching step or conditioning step to provide a positive color image in color reversal films. Motion picture films and prints may include still other processing steps. However, all of these steps and the conventional components of the processing compositions are well known, as described for example, in *Research Disclosure* publication 308119, December 1989, publication 17643, December 1978, and publication 38957, September, 1996. *Research Disclosure* is a publication of Kenneth Mason Publications Ltd., Dudley House, 12 North Street, Emsworth, Hampshire PO10 7DQ England (or Emsworth Design Inc., 121 West 19th street, New York, N.Y. 10011). Some additional details are provided below in describing such compositions, but additional details can be supplied from the many publications listed in the noted *Research Disclosure* publication.

The spectral sensitizing dyes typically present in color photographic materials are described in numerous publications including for example, U.S. Pat. No. 5,747,236 (Farid et al.), incorporated herein by reference for its teaching about spectral sensitizing dyes. Classes of such dyes include, but are not limited to, cyanines and merocyanines.

The concentrated aqueous color developing compositions of this invention include only two essential components, that is one or more color developing agents (in free base form) and one or more of the compounds represented by Structure I. However, in some embodiments, the concentrated compositions may include one or more antioxidants (including sulfites and organic antioxidants such as hydroxylamine and its derivatives), and organic solvents (described below). In still other embodiments, various other conventional addenda including metal ion sequestering agents, corrosion inhibitors, and buffers may be present to provide a "single-part" concentrated color developing composition.

Where the concentrated composition includes only some of the noted components, color development may require the use of additional "parts" or solutions that include the additional chemical components. The various "parts" (including the concentrated composition of this invention) can then be combined in a suitable manner to achieve the desired photoprocessing result.

Most of the components of the one or more "parts" can be present in conventional amounts unless otherwise noted herein. For example, the color developing agent is generally present in an amount of at least 0.08 mol/l (preferably at least 0.1 mol/l), and an antioxidant or preservative for the color developing agent is generally present in an amount of at least 0.01 mol/l (preferably at least 0.2 mol/l). The compound of Structure I can be present in an amount of at least 0.009 mol/l (and preferably from about 0.009 to about 0.2 mol/l). The pH of the concentrated composition is generally from about 11 to about 13, and preferably from about 12 to about 12.5.

Exemplary color developing composition components (except the sensitizing dye stain reducing agents described herein) are described for example, in EP-A-0 530 921 (Buongiorne et al.), U.S. Pat. No. 5,037,725 (Cullinan et al.), U.S. Pat. No. 5,552,264 (Cullinan et al.), U.S. Pat. No. 5,508,155 (Marrese et al.), U.S. Pat. No. 4,892,804 (Vincent et al.), U.S. Pat. No. 4,482,626 (Twist et al.), U.S. Pat. No. 4,414,307 (Kapecki et al.), U.S. Pat. No. 4,876,174 (Ishikawa et al.), U.S. Pat. No. 5,354,646 (Kobayashi et al.), and U.S. Pat. No. 4,264,716 (Vincent et al.), all incorporated herein for their teaching about color developing compositions.

Useful preservatives in the color developing compositions include sulfites (such as sodium sulfite, potassium sulfite, sodium bisulfite and potassium metabisulfite), and various organic antioxidants including, but not limited to, hydroxylamines and its derivatives (especially those derivatives having substituted or unsubstituted alkyl or aryl groups), hydrazines, hydrazides, amino acids, ascorbic acid (and derivatives thereof), hydroxamic acids, aminoketones, mono- and polysaccharides, mono- and polyamines, quaternary ammonium salts, nitroxy radicals, alcohols, and oximes. More particularly useful hydroxylamine derivatives include substituted and unsubstituted monoalkyl- and dialkylhydroxylamines (especially those substituted with sulfo, carboxy, phospho, hydroxy, carbonamido, sulfonamido or other solubilizing groups). Mixtures of compounds from the same or different classes of antioxidants can also be used if desired.

Examples of useful antioxidants derived from hydroxylamine are described for example, in U.S. Pat. No. 4,892,804 (noted above), U.S. Pat. No. 4,876,174 (noted above), U.S. Pat. No. 5,354,646 (noted above), U.S. Pat. No. 5,660,974 (Marrese et al.), U.S. Pat. No. 5,709,982 (Marrese et al.), and U.S. Pat. No. 5,646,327 (Burns et al.), the disclosures of which are all incorporated herein by reference for description of useful organic antioxidants. Many of these antioxidants are mono- and dialkylhydroxylamines that are unsubstituted or substituted with one or more substituents on one or both alkyl groups as noted above. For example, the noted hydroxylamine derivatives can be mono- or dialkylhydroxylamines having one or more sulfo, carboxy, phospho, or hydroxy substituents on the one or more alkyl groups.

Particularly useful color developing agents include aminophenols, p-phenylenediamines (especially N,N-dialkyl-p-phenylenediamines) and others which are well known in the art, such as EP 0 434 097A1 (published Jun. 26, 1991) and EP 0 530 921A1 (published Mar. 10, 1993). The color developing agents are present in "free base form" as opposed to being salts.

Preferred color developing agents include, but are not limited to, the following compounds in "free base form": N,N-diethyl p-phenylenediamine sulfate (KODAK Color Developing Agent CD-2), 4-amino-3-methyl-N-(2-methane sulfonamidoethyl)aniline sulfate, 4-(N-ethyl-N-β-hydroxyethylamino)-2-methylaniline sulfate (KODAK Color Developing Agent CD-4), p-hydroxyethylethylaminoaniline sulfate, 4-(N-ethyl-N-2-methanesulfonylaminoethyl)-2-methylphenylenediamine sesquisulfate (KODAK Color Developing Agent CD-3), 4-(N-ethyl-N-2-methanesulfonylaminoethyl)-2-methylphenylenediamine sesquisulfate, and others readily apparent to one skilled in the art. A most preferred color developing agent is KODAK Color Developing Agent CD-3 for the processing of color reversal materials.

An essential component of the concentrated photographic color developing compositions of this invention is a spectral sensitizing dye stain reducing agent that is a 2,6-dinaphthylaminotriazine compound as represented by Structure I (or mixture thereof). These compounds have at least four sulfonate solubilizing groups attached to the naphthyl rings and specific substituents attached to the triazine ring.

The compounds useful in this invention can be represented by Structure I:

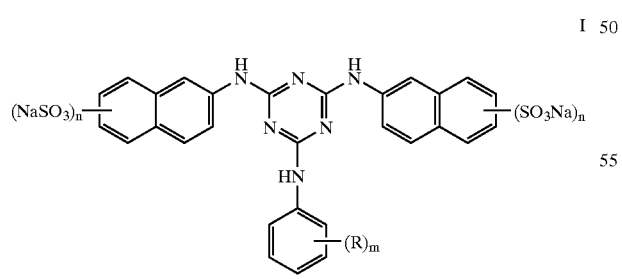

I wherein R is carboxy (or salt thereof) or sulfo (or salt thereof), m is an integer of from 0 to 5, and n is an integer of from 2 to 7. Preferably, R is carboxy, m is an integer of 1 to 2, and n is 2.

Representative compounds within Structure I are the following Compounds I-1 to I-7:

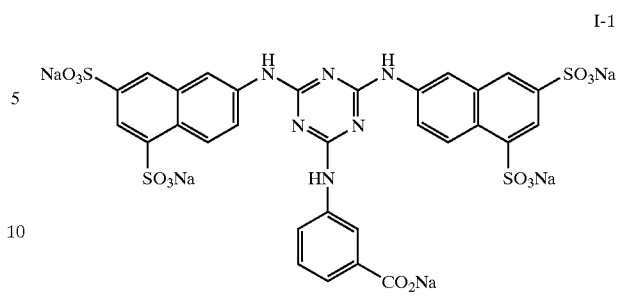

I-1

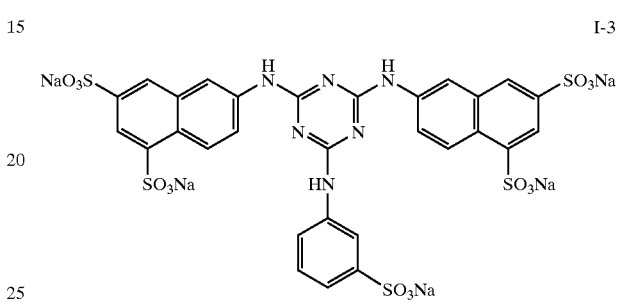

I-3

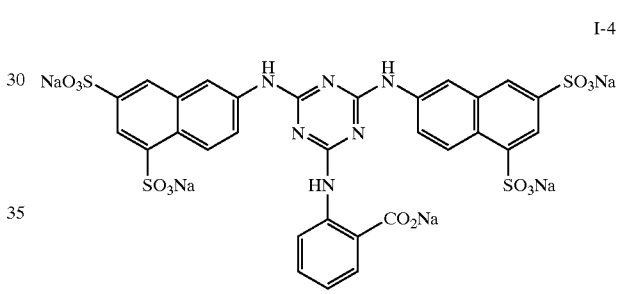

I-4

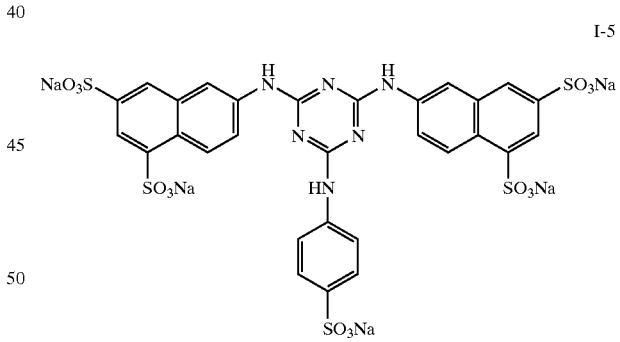

I-5

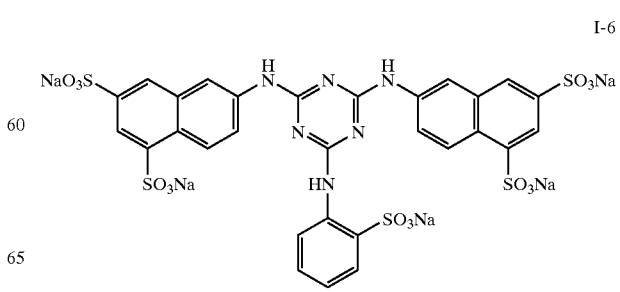

I-6

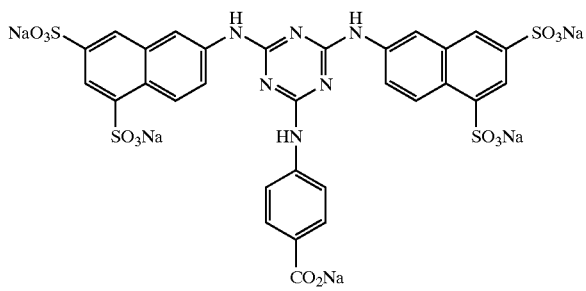

I-7

Single compounds or mixtures thereof can also been used in the practice of this invention. Compound I-1 (or an alkali metal salt thereof) noted above is most preferred.

These 2,6-dinaphthylamninotriazine compounds can be prepared using the methods described for example in WO 97/10887. A representative synthesis of preferred Compound I-1 is provided below.

Buffering agents are generally present in the concentrated aqueous color developing compositions of this invention to provide or maintain desired alkaline pH. These buffering agents are preferably soluble in the organic solvent described below and have a pKa of from about 9 to about 13. Such useful buffering agents include, but are not limited to carbonates, borates, tetraborates, glycine salts, triethanolamine, diethanolamine, phosphates and hydroxybenzoates. Alkali metal carbonates (such as sodium carbonate, sodium bicarbonate and potassium carbonate) are preferred buffering agents. Mixtures of buffering agents can be used if desired.

In addition to buffering agents, pH can also be raised or lowered to a desired value using one or more acids or bases. It may be particularly desirable to raise the pH by adding a base, such as a hydroxide (for example sodium hydroxide or potassium hydroxide).

An optional but preferred component of the concentrated aqueous color developing compositions of this invention is a photographically inactive, water-miscible or water-soluble, straight-chain organic solvent that is capable of dissolving color developing agents in their free base forms. Such organic solvents can be used singly or in combination, and preferably each has a molecular weight of at least 50, and preferably at least 100, and generally 200 or less and preferably 150 or less. Such preferred solvents generally have from 2 to 10 carbon atoms (preferably from 2 to 6 carbon atoms, and more preferably from 4 to 6 carbon atoms), and can additionally contain at least two nitrogen or oxygen atoms, or at least one of each heteroatom. The organic solvents are substituted with at least one hydroxy functional group, and preferably at least two of such groups. They are straight-chain molecules, not cyclic molecules.

By "photographically inactive" is meant that the organic solvents provide no substantial positive or negative effect upon the color developing function of the concentrate.

Useful organic solvents include, but are not limited to, polyols including glycols (such as ethylene glycol, diethylene glycol and triethylene glycol), polyhydroxyamines (including polyalcoholamines), and alcohols (such as ethanol and benzyl alcohol). Glycols are preferred with ethylene glycol, diethylene glycol and triethylene glycol being most preferred. Of the alcohols, ethanol and benzyl alcohol are most preferred. The most preferred organic solvent is diethylene glycol.

Other optional but desirable component(s) of the concentrated aqueous color developing composition of this invention is a polyphosphonic acid (or salt thereof) as a calcium ion sequestering agent. A mixture of such compounds can be used if desired. Suitable salts include ammonium and alkali metal ions salts.

Preferred compounds of this nature can be represented by the following Structure II:

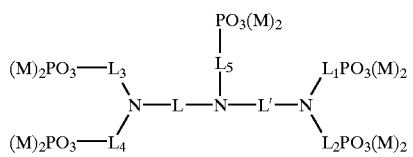

II wherein L, L', $L_1$, $L_2$, $L_3$, $L_4$ and $L_5$ are independently substituted or unsubstituted divalent aliphatic linking groups, each independently having 1 to 4 carbon, oxygen, sulfur or nitrogen atoms in the linking group chain. Preferably, these substituted or unsubstituted divalent linking groups have 1 to 4 carbon atoms in the linking group chain (such as substituted or unsubstituted branched or linear alkylene groups). More preferably, the divalent linking groups are independently substituted or unsubstituted methylene or ethylene. Most preferably, L and L' are each substituted or unsubstituted ethylene (preferably unsubstituted), and each of the other linking groups is an unsubstituted methylene group. M is hydrogen or a monovalent cation (such as ammonium ion or an alkali metal salt).

The noted divalent groups can be substituted with any substituent that does not interfere with the desired performance of the sequestering agent, or with the photochemical properties of the concentrated aqueous color developing compositions. Such substituents include, but are not limited to, hydroxy, sulfo, carboxy, halo, lower alkoxy (1 to 3 carbon atoms) or amino.

Mixtures of these sequestering agents can be used if desired. A particularly useful one is diethylenetriaminepentamethylenephosphonic acid or an alkali metal salt thereof (available as DEQUEST™ 2066 from Solutia Co.).

Still other useful polyphosphonic acid sequestering agent are hydroxyalkylidene diphosphonic acids (or salts thereof). Mixtures of such compounds can be used if desired. Useful salts include the ammonium and alkali metal ion salts.

Preferred hydroxyalkylidene diphosphonic acids (or salts thereof) can be represented by the following Structure III:

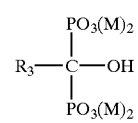

III wherein $R_3$ is a substituted or unsubstituted alkyl group having 1 to 5 carbon atoms (methyl, methoxymethyl, ethyl, isopropyl, n-butyl, t-butyl and n-pentyl) and M is hydrogen or a monovalent cation (such as ammonium or alkali metal ions). Preferably, $R_3$ is methyl or ethyl, and most preferably, it is ethyl.

Representative sequestering agents of this class include, but are not limited to, 1-hydroxyethylidene-1,1'-diphosphonic acid, 1-hydroxy-n-propylidene-1,1 - diphosphonic acid, 1-hydroxy-2,2-dimethylpropylidene- 1,1-diphosphonic acid and others that would be readily apparent to one skilled in the art (and alkali metal and ammonium salts thereof). The first compound is most preferred and is available as DEQUEST™ 2010. Its tetrasodium salt is available as DEQUEST™ 2016D. Both materials are available from Solutia Co.

One particularly useful combination of polyphosphonic acid sequestering agents is 1-hydroxyethylidene-1,1'-diphosphonic acid (or a salt thereof) and diethylenetriaminepentamethylenephosphonic acid (or a salt thereof), as described in U.S. Ser. No. 09/438,121 (filed Nov. 10, 1999 by Haye et al.).

Still another useful combination of polyphosphonic acid sequestering agents is diethylenetriaminepentamethylenephosphonic acid (or a salt thereof) and morpholinomethanediphosphonic acid (or a salt thereof) as described in U.S. Ser. No. 09/804,339 (filed Mar. 13, 2001 by Haye et al.) as a CIP of U.S. Ser. No. 09/438,121 (noted above).

In addition, morpholinomethanediphosphonic acid (or a salt thereof) can be used as the sole polyphosphonic acid sequestering agent as noted also in U.S. Ser. No. 09/804,339 (noted above).

It is also possible to include other metal ion sequestering agents (for example, for iron, copper or manganese ion sequestration) in the color developing composition as long as the other conditions of the invention are met.

The concentrated aqueous color developing compositions of this invention can also include one or more of a variety of other addenda that are commonly used in photographic color developing compositions, including alkali metal halides (such as potassium chloride, potassium bromide, sodium bromide and sodium iodide), auxiliary co-developing agents (such as phenidone type compounds particularly for black and white developing compositions), antifoggants, development accelerators, wetting agents, fragrances, stain reducing agents, surfactants, defoaming agents, and water-soluble or water-dispersible color couplers, as would be readily understood by one skilled in the art [see for example, *Research Disclosure* publications noted above]. The amounts of such additives are well known in the art also.

As noted above, the photographic spectral sensitizing dye stain reducing agents described herein can be used individually or in a mixture in the concentrated aqueous color developing compositions. Generally, such processing compositions can be used diluted or undiluted to provide a color image in imagewise exposed photographic silver halide materials, including but not limited to, color reversal films, color negative films, color papers (including positive and negative color papers), motion imaging films and prints (including intermediate films). Such films and papers are well known in the art, having been described in hundreds of publications in various countries of the world, and being commercialized as dozens of different products from several manufacturing companies such as Eastman Kodak Company, Konica Photo Co., Fuji Photo Co, AGFA, and Sakura.

Generally, in the processing of color photographic materials to provide color images, the materials are imagewise exposed in a suitable fashion using a suitable imaging source (tungsten lamps, sunlight, lasers and phosphors). The imagewise exposed materials are then processed in a series of wet photographic processing baths in a suitable sequence of steps to initiate various chemical reactions in the silver halide and color-forming materials to generate the desired images.

Color developing is generally followed by one or more steps for desilvering. Generally, this includes at least one photographic bleaching or bleach-fixing step. Useful photographic bleaching compositions generally include one or more persulfate, peracid (such as hydrogen peroxide, periodates or percarbonates) or high metal valent ion bleaching agents, such as iron(II) complexes with simple anions (such as nitrate, sulfate, and acetate), or with carboxylic acid or phosphonic acid ligands. Particularly useful bleaching agents include iron complexes of one or more aminocarboxylic acids, aminopolycarboxylic acids, polyaminocarboxylic acids or polyaminopolycarboxylic acids, or salts thereof. Particularly useful chelating ligands include conventional polyaminopolycarboxylic acids including ethylenediaminetetraacetic acid and others described in *Research Disclosure*, noted above, U.S. Pat. No. 5,582,958 (Buchanan et al.) and U.S. Pat. No. 5,753,423 (Buongiorne et al.). Biodegradable chelating ligands are also desirable because the impact on the environment is reduced. Useful biodegradable chelating ligands include, but are not limited to, iminodiacetic acid or an alkyliminodiacetic acid (such as methyliminodiacetic acid), ethylenediaminedisuccinic acid and similar compounds as described in EP-A-0 532,003, and ethylenediamine monosuccinic acid and similar compounds as described in U.S. Pat. No. 5,691,120 (Wilson et al.), all of which are incorporated herein by reference in relation to their description of bleaching agents.

These and many other such iron complexing ligands known in the art including those described in U.S. Pat. No. 4,839,262 (Schwartz), U.S. Pat. No. 4,921,779 (Cullinan et al.), U.S. Pat. No. 5,037,725 (noted above), U.S. Pat. No. 5,061,608 (Foster et al.), U.S. Pat. No. 5,334,491 (Foster et al.), U.S. Pat. No. 5,523,195 (Darmon et al.), U.S. Pat. No. 5,582,958 (Buchanan et al.), U.S. Pat. No. 5,552,264 (noted above), U.S. Pat. No. 5,652,087 (Craver et al.), U.S. Pat. No. 5,928,844 (Feeney et al.) U.S. Pat. No. 5,652,085 (Wilson et al.), U.S. Pat. No. 5,693,456 (Foster et al.), U.S. Pat. No. 5,834,170 (Craver et al.), and U.S. Pat. No. 5,585,226 (Strickland et al.), all incorporated herein by reference for their teaching of bleaching compositions. The useful amounts of bleaching agent(s) in the composition are well known in the art. These bleaching agents are also useful in bleach-fixing compositions.

Other components of the bleaching solution can include buffers, halides, corrosion inhibiting agents, and metal ion sequestering agents. These and other components and conventional amounts are described in the references in the preceding paragraph. The pH of the bleaching composition is generally from about 4 to about 6.5.

Photographic fixing compositions are also useful for individual fixing steps of photographic processing compositions.

Useful fixing agents for photographic fixing compositions are well known. Examples of photographic fixing agents include, but are not limited to, thiosulfates (for example sodium thiosulfate, potassium thiosulfate and ammonium thiosulfate), thiocyanates (for example sodium thiocyanate, potassium thiocyanate and ammonium thiocyanate), thioethers (such as ethylenebisthioglycolic acid and 3,6-dithia-1,8-octanediol), imides and thiourea. Thiosulfates and thiocyanates are preferred, and thiosulfates are more preferred. Ammonium thiosulfate is most preferred. The amounts of total fixing agents in the fixing compositions are also well known. These fixing agents are also useful in bleach-fixing compositions.

It is also known to use fixing accelerators in fixing compositions. Representative fixing accelerators include, but are not limited to, ammonium salts, guanidine, ethylenediamine and other amines, quaternary ammonium salts and other amine salts, thiourea, thioethers, thiols and thiolates. Examples of useful thioether fixing accelerators are described in U.S. Pat. No. 5,633,124 (Schmittou et al.), incorporated herein for the teaching of fixing compositions.

The fixing compositions generally contain one or more monovalent or divalent cations supplied by various salts used for various purposes (for example, salts of fixing agents). It is preferred that the cations be predominantly ammonium cations, that is at least 50% of the total cations are ammonium ions. Such fixing compositions are generally known as "high ammonium" fixing compositions.

The fixing compositions can also include one or more of various addenda optionally but commonly used in such compositions for various purposes, including hardening agents, preservatives (such as sulfites or bisulfites), metal sequestering agents (such as polycarboxylic acids and organophosphonic acids), buffers, and fixing accelerators. The amounts of such addenda in the working strength compositions would be readily known to one skilled in the art.

The desired pH of the fixing compositions is 8 or less, and can be achieved and maintained using any useful combination of acids and bases, as well as various buffers.

Other details of fixing compositions not explicitly described herein are considered well known in the art, and are described for example, in *Research Disclosure* publication 38957 (noted below), and publications noted therein in paragraph XX(B), U.S. Pat. No. 5,424,176 (Schmittou et al.), U.S. Pat. No. 4,839,262 (noted above), U.S. Pat. No. 4,921,779 (noted above), U.S. Pat. No. 5,037,725 (noted above), U.S. Pat. No. 5,523,195 (noted above), U.S. Pat. No. 5,552,264 (noted above), all incorporated herein by reference for their teaching of fixing compositions.

Another useful photographic processing composition is a dye stabilizing composition containing one or more photographic imaging dye stabilizing compounds. Such compositions can be used at the end of the processing sequence (such as for color negative films and color papers), or in another part of the processing sequence (such as between color development and bleaching as a pre-bleaching composition).

Such dye stabilizing compositions generally have a pH of from about 5.5 to about 8, and include a dye stabilization compound (such as an alkali metal formaldehyde bisulfite, hexamethylenetetramine, various benzaldehyde compounds, and various other formaldehyde releasing compounds), buffering agents, bleach-accelerating compounds, secondary amines, preservatives, and metal sequestering agents. All of these compounds and useful amounts are well known in the art, including U.S. Pat. No. 4,839,262 (Schwartz), U.S. Pat. No. 4,921,779 (noted above), U.S. Pat. No. 5,037,725 (noted above), U.S. Pat. No. 5,523,195 (noted above), and U.S. Pat. No. 5,552,264 (noted above), all incorporated herein by reference for their teaching of dye stabilizing compositions, A preferred dye-stabilizing composition includes sodium formaldehyde bisulfite as a dye stabilizing compound, and thioglycerol as a bleach-accelerating compound. More preferably, this composition is used as a pre-bleaching composition during the processing of color reversal photographic materials.

In some processing embodiments of this invention, a dye stabilizing composition or final rinsing composition is used to clean the processed photographic material as well as to stabilize the color image. Either type of composition generally includes one or more anionic, nonionic, cationic or amphoteric surfactants, and in the case of dye stabilizing compositions, one or more dye stabilizing compounds as described above. Particularly useful dye stabilizing compounds useful in these dye stabilizing compositions are described for example in EP-A-0 530 832 (Koma et al.) and U.S. Pat. No. 5,968,716 (McGuckin et al.). Other components and their amounts for both dye stabilizing and final rinsing compositions are described in U.S. Pat. No. 5,952,158 (McGuckin et al.), U.S. Pat. No. 3,545,970 (Giorgianni et al.), U.S. Pat. No. 3,676,136 (Mowrey), U.S. Pat. No. 4,786,583 (Schwartz), U.S. Pat. No. 5,529,890 (McGuckin et al.), U.S. Pat. No. 5,578,432 (McGuckin et al.), U.S. Pat. No. 5,534,396 (noted above), U.S. Pat. No. 5,645,980 (McGuckin et al.), U.S. Pat. No. 5,667,948 (McGuckin et al.), U.S. Pat. No. 5,750,322 (McGuckin et al.) and U.S. Pat. No. 5,716,765 (McGuckin et al.), all of which are incorporated by reference for their teaching of such compositions.

Representative sequences for processing various color photographic materials are described for example in *Research Disclosure* publication 308119, December 1989, publication 17643, December 1978, and publication 38957, September 1996.

As noted above, the concentrated aqueous color developing compositions of the present invention are used to process color photographic elements, and particularly color photographic papers. The general sequence of steps and conditions (times and temperatures) for processing are well known as Process C-41 and Process ECN-2 for color negative films, Process E-6 and Process K-14 for color reversal films, Process ECP for color prints, and Process RA-4 for color papers.

Color papers that can be processed using the compositions of this invention include, but are not limited, KODAK EKTACOLOR EDGE V, VII and VIII Color Papers (Eastman Kodak Company), KODAK ROYAL VII Color Papers (Eastman Kodak Company), KODAK PORTRA III, IIIM Color Papers (Eastman Kodak Company), KODAK SUPRA III and IIIM Color Papers (Eastman Kodak Company), KODAK ULTRA III Color Papers (Eastman Kodak Company), FUJI SUPER Color Papers (Fuji Photo Co., FA5, FA7 and FA9), FUJI CRYSTAL ARCHIVE and Type C Color Papers (Fuji Photo Co.), KONICA COLOR QA Color Papers (Konica, Type QA6E and QA7), and AGFA TYPE II and PRESTIGE Color Papers (AGFA). The compositions and constructions of such commercial color photographic elements would be readily determined by one skilled in the art.

KODAK DURATRANS, KODAK DURACLEAR, KODAK EKTAMAX RAL, and KODAK DURAFLEX photographic materials and KODAK Digital Paper Type 2976 can also be processed using the present invention.

The various processing steps, including color developing, bleaching, fixing (or bleach-fixing), and rinsing/stabilizing can be carried out using single working strength composition baths (single stage), or multistage systems having multiple baths of the same processing composition. Agitation or recirculation can also be used in one or more steps if desired. Processing can also be carried out using any known method. Such methods include, but are not limited to, immersing the photographic element in a working strength composition, laminating a cover sheet containing the composition to the photographic element, or applying the composition by high velocity jet or spraying.

Preferably, in some applications, color development is carried out using the concentrated aqueous color developing composition of this invention that has been diluted up to 15 times with water or a suitable buffer, and preferably from 7 to 10 times to provide a working strength or color developing replenishing composition. Dilution can be carried out during or prior to its use in the image formation process. Alternatively, the concentrated color developing composition can be added directly, without dilution, to the working strength color development bath or to a color development replenisher.

Color development is generally carried out for conventional times and under conventional conditions. In addition, the concentrated aqueous color developing compositions of this invention can be used in what would be considered "rapid" processing wherein the color developing step is carried for as little as 120 seconds. More generally, color development is usually carried out for from about 30 to about 90 seconds.

Processing can be carried out using any suitable processing equipment, including deep tank processors, and "low volume thin tank" processes including rack and tank and automatic tray designs, as described for example in U.S. Pat. No. 5,436,118 (Carli et al.) and publications noted therein. Thus, processing can be carried out in large-scale processing labs, or in what are known as "mini-labs" that are normally placed in smaller environments. Rotary tube processors can also be used for processing photographic materials.

The following synthetic procedure and examples are provided to illustrate the invention, and not to be limiting in any fashion.

Preparation of Compound I-1

Cyanuric chloride (133.0 g, 0.72 mole) was dissolved in 3 liters of acetone in a 12-liter flask equipped with a mechanical stirrer. Crushed ice (3 kg) was added to it. To this cold mixture was added all at once, while stirring, a solution containing 6-amino-1,3-naphthalenedisulfonic acid disodium salt (605 g, 88% purity, 1.53 mole) in 1800 ml water and 1200 g of ice. An aqueous solution (200 ml) of sodium hydroxide (57.6 g, 1.44 mole) was added portion-wise with stirring to the resulting mixture, as the reaction pH became acidic. The first 100 ml portion was added over 15 minutes while the reaction temperature was still less than 0° C. This reaction mixture was then heated gradually by using a steam bath. The remaining 100 ml were added gradually over the next 1.25 hours while the reaction temperature was raised to 60° C. The reaction mixture was stirred at 60° C. for an additional 2 hours and was then cooled to room temperature.

The resulting reaction mixture was slowly poured into a solvent mixture containing 60 liters of acetone and 6 liters of methanol, while stirring. It was then allowed to settle overnight and 40 liters of solvent was removed by decanting. The resulting solid was collected on an 11.5 inch (29.2 cm) diameter funnel using a VWR#413 filter paper. The solid was then washed with acetone and P950 ligroin, and was air-dried on the funnel. The resulting solid clumps were crushed and the powder was dried in a vacuum oven overnight, giving rise to 560 g (yield: 96.5%) of the desired chloro intermediate.

Sodium bicarbonate (118 g, 1.4 mole) was added to 2.5 liters of water in a 5-liter flask. 3-Aminobenzoic acid (92 g, 0.67 mole) was added portion-wise to this solution while being heated to 85° C. The chloro intermediate prepared as described above (550 g, 0.68 mole) was added to this solution portion-wise over a period of 15 minutes. The resulting mixture was heated at 85–90° C. overnight. It was then allowed to cool to room temperature overnight. Small amounts of insoluble materials were filtered off using a glass-fiber filter paper. The filtrate was poured into 11 liters of acetone. It was stirred for 5 minutes and was allowed to settle. The clear acetone supernatant was decanted off. The resulting amber oil was added to a mixture of 25 liters of acetone and 2.5 liters of methanol, and was stirred for 10 minutes. The resulting solid was collected on an 11.5 inch (29.2 cm) diameter funnel using a VWR #413 filter paper. The resulting solid was first washed with a mixture containing 10:1 acetone: methanol (5 liters), then with acetone (5 liters), and finally with P950 ligroin (5 liters). The solid was then air-dried on the funnel. The solid clumps were crushed and the powder was dried in a vacuum oven at 50° C. for 2 days, giving rise to 547 g (yield: 87.8%) of the desired Compound I-1.

EXAMPLE 1

Preferred Single-part Concentrated Color Developing Composition

A concentrated aqueous color developing composition of this invention was prepared by mixing the following components:

| | |
|---|---|
| Demineralized water | 49.8 g |
| DEQUEST 2010 (60%) | 0.55 g |
| Potassium carbonate (47%) | 353 g |
| Potassium bicarbonate | 14.6 g |
| Potassium bromide | 0.19 g |
| Compound I-1 (noted above) | 8.5 g |
| Triethanolamine (85%) | 23.0 g |
| DEQUEST 2066 (25%) | 40.0 g |
| Diethylene glycol | 129 g |
| "Premix solution" (see below) | 603 g |
| pH of 12.1 | |
| Premix Solution: | |
| Demineralized water | 84.2 g |
| Sodium hydroxide (50%) | 56.1 g |
| N,N-diethylhydroxylamine (85%) | 75.8 g |
| KODAK Color Developing Agent CD-3 | 95.5 g |
| Diethylene glycol | 878 g |

The color developing agent was present in "free base form" since the Premix Solution contained sodium hydroxide base.

Samples (100 ml) of this concentrated aqueous color developing composition were incubated individually at −35° C., −18° C., −7° C., −1° C., 4° C., and 10° C. for 14 days and then any physical changes (such as precipitation) were observed 24 hours thereafter. No precipitates were observed in any of the samples.

EXAMPLE 2

Concentrated Color Developing Composition for Use in Multi-part Color Development Kit The following Part A was prepared according to the present invention by mixing the components in the noted order:

| | |
|---|---|
| Water (demineralized) | 100 g |
| Sodium hydroxide (50%) | 73.1 g |
| N,N'-diethylhydroxylamine (85%) | 30.6 g |
| Kodak Color Developing Agent CD-3 | 126 g |
| Diethylene glycol | 650 g |
| Compound I-1 (noted above) | 10.6 g |
| Diethylene glycol | 189 g |
| pH of 12.4 | |

The color developing agent was present in "free base form" since the Part A solution contained sodium hydroxide base.

The concentrated composition was subjected to stability tests as described in Example 1. No precipitates were observed in any of the samples.

To use this concentrated composition (Part A) of the present invention in photographic processing of color papers, it can be mixed with second (Part B) and third (Part C) solutions having the following compositions at a volume ratio of 0.51:0.54:0.28 (A:B:C).

Part C:

| | |
|---|---|
| Potassium carbonate (47.5%) | 593 g |
| DEQUEST ™ 2066 sequestering agent (25%) | 57.8 g |
| Water | 552 g |
| Triethanolamine (85%) | 21.2 g |
| pH to 12.4 using potassium hydroxide | |
| Part C: | |
| DEQUEST ™ 2010 sequestering agent (60%) | 4.5 g |
| Water | 984 g |
| pH to 12.4 using potassium hydroxide. | |

The invention has been described in detail with particular reference to preferred embodiments thereof, but it will be understood that variations and modifications can be effected within the spirit and scope of the invention.

What is claimed is:

1. A concentrated aqueous color developing composition having a pH of from about 11 to about 13 and comprising:

a) at least 0.08 mol/l of a color developing agent in free base form, and b) at least 0.009 mol/l of a compound having the Structure I:

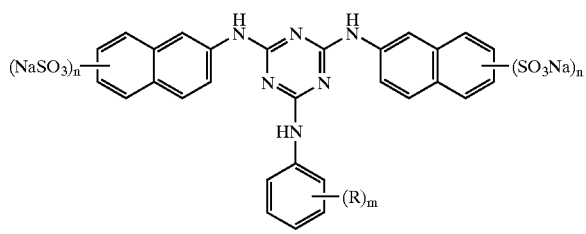

wherein R is carboxy or sulfo, m is an integer of from 0 to 5, and n is an integer of from 2 to 7.

2. The composition of claim 1 wherein said compound of Structure I is present in an amount of from about 0.009 to about 0.02 mol/l.

3. The composition of claim 1 wherein R is carboxy, m is 1 or 2, and n is 2.

4. The composition of claim 1 wherein said compound of Structure I is:

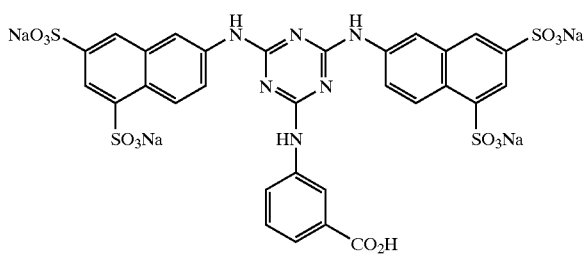

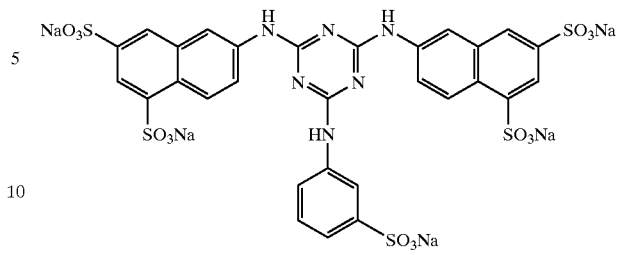

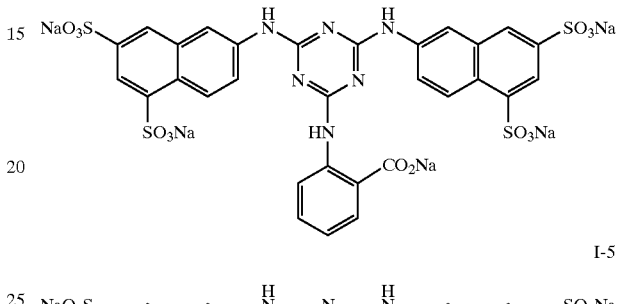

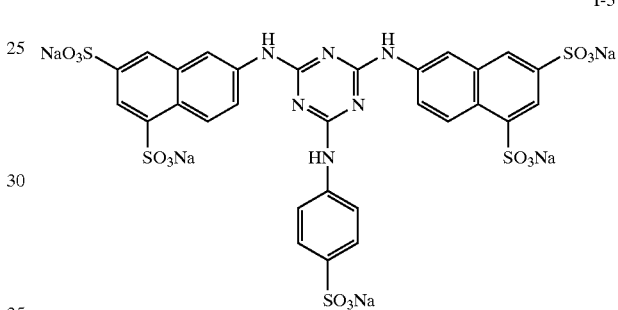

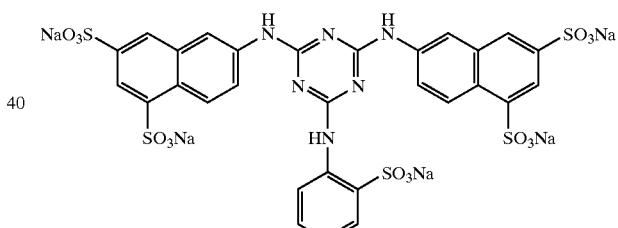

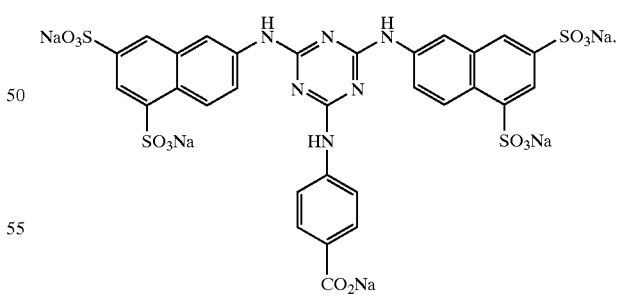

5. The composition of claim 1 wherein said compound of Structure I is Compound I-1.

6. The composition of claim 1 having a pH of from about 12 to about 12.5, and wherein said color developing agent in free base form is present in an amount of at least 0.1 mol/l.

7. The composition of claim 1 further comprising at least 0.1 mol/l of an antioxidant.

8. The composition of claim 7 comprising an organic antioxidant.

9. The composition of claim 1 further containing a metal ion sequestering agent, buffer, or water-soluble or water-miscible organic solvent.

10. The composition of claim 9 further containing diethylene glycol, ethylene glycol, or triethylene glycol.

11. The composition of claim 9 further containing a carbonate buffer.

12. The composition of claim 9 further containing a polyphosphonic acid (or salt thereof) sequestering agent.

13. The composition of claim 1 wherein said color developing agent is 4-(N-ethyl-N-2-methanesulfonylaminoethyl)-2-methylphenylenediamine sesquisulfate, in free base form.

14. A method for providing a color image comprising color developing an imagewise exposed color silver halide photographic material using the concentrated color developing composition of claim 1 with or without dilution.

15. The method of claim 14 further comprising desilvering said color silver halide photographic material.

16. The method of claim 14 wherein color developing is carried out within 120 seconds.

17. The method of claim 16 wherein color developing is carried out for from about 30 to about 90 seconds.

18. The method of claim 14 wherein said color silver halide photographic material is a color paper.

* * * * *